United States Patent
Magna et al.

(10) Patent No.: US 10,544,069 B2
(45) Date of Patent: Jan. 28, 2020

(54) METHOD FOR DIMERIZATION OF ETHYLENE COMPRISING A STEP FOR TREATMENT OF THE REACTION EFFLUENT

(71) Applicant: IFP Energies Nouvelles, Rueil-Malmaison (FR)

(72) Inventors: Lionel Magna, Lyons (FR); Aurelie Camarata, Mions (FR)

(73) Assignee: IFP Energies Nouvelles, Rueil-Malmaison (FR)

( * ) Notice: Subject to any disclaimer, the term of this patent is extended or adjusted under 35 U.S.C. 154(b) by 0 days.

(21) Appl. No.: 16/208,749

(22) Filed: Dec. 4, 2018

(65) Prior Publication Data
US 2019/0169085 A1 Jun. 6, 2019

(30) Foreign Application Priority Data

Dec. 5, 2017 (FR) ..................................... 17 61630

(51) Int. Cl.
| | | |
|---|---|---|
| *C07C 2/24* | (2006.01) |
| *C07C 2/26* | (2006.01) |
| *C07C 2/30* | (2006.01) |
| *C07C 2/32* | (2006.01) |
| *C07C 11/08* | (2006.01) |
| *C07C 7/10* | (2006.01) |
| *B01J 31/38* | (2006.01) |

(52) U.S. Cl.
CPC .................. *C07C 2/32* (2013.01); *C07C 7/10* (2013.01); *C07C 11/08* (2013.01); *B01J 31/38* (2013.01); *B01J 2531/31* (2013.01); *B01J 2531/46* (2013.01)

(58) Field of Classification Search
CPC .... C07C 2/24; C07C 2/26; C07C 2/30; C07C 2/32; C07C 2/34
USPC .......................................... 585/511, 512, 513
See application file for complete search history.

(56) References Cited

U.S. PATENT DOCUMENTS

| | | |
|---|---|---|
| 5,030,790 A | 7/1991 | Sergienko et al. |
| 2018/0258009 A1 * | 9/2018 | Alqahtani ................. C07C 2/22 |

FOREIGN PATENT DOCUMENTS

| | | |
|---|---|---|
| EP | 0221206 A1 | 5/1987 |
| EP | 0358763 A1 | 3/1990 |
| SU | 459451 A1 | 2/1975 |

OTHER PUBLICATIONS

French Search Report dated Jun. 29, 2018 issued in corresponding FR 1761630 application (2 pages).

* cited by examiner

*Primary Examiner* — Thuan D Dang
(74) *Attorney, Agent, or Firm* — Millen, White, Zelano & Branigan, PC

(57) ABSTRACT

The invention describes a method for dimerization of ethylene implementing a step for treatment of raw effluent by neutralization, at the outlet of the reactor, of the catalyst for dimerization of ethylene into but-1-ene by a particular alcohol.

18 Claims, No Drawings

METHOD FOR DIMERIZATION OF ETHYLENE COMPRISING A STEP FOR TREATMENT OF THE REACTION EFFLUENT

TECHNICAL FIELD OF THE INVENTION

The invention relates to the dimerization of ethylene into but-1-ene, and in particular a method for treatment of the effluent that is obtained directly from the dimerization of ethylene into but-1-ene.

The object of this invention is the improvement in performance of a method for dimerization of ethylene by achieving an increased purity of but-1-ene by implementing a step for treatment of the raw effluent by neutralization, at the reactor outlet, of the catalyst for dimerization of ethylene into but-1-ene.

PRIOR ART

The dimerization of ethylene into but-1-ene by the use of a homogeneous catalyst based on a transition metal, combined with an aluminum-based activator, has been studied since the 1970s.

In particular, it is possible to cite the methods for dimerization of ethylene into but-1-ene implementing a catalytic system that is obtained by the interaction of a titanium precursor and an alkylaluminum, described in the patent U.S. Pat. No. 2,943,125, and in the application FR2552079. One drawback of these methods is the formation of significant amounts of by-products that are obtained from secondary reactions that brings about a reduction in the selectivity of but-1-ene.

In the case of the industrial practice of a method such as those described here and that use a homogeneous catalysis technique, in addition to the reaction itself, the problem of separation and isolation of the desired product from the raw reaction mixture arises. The latter contains in particular the catalyst that is in principle soluble in the reaction medium. It is therefore necessary to ensure that the presence of this catalyst residue does not alter, by uncontrolled reaction, the purity of the initial reaction. In particular, it is necessary to ensure that the methods for purification downstream from the reactor do not degrade the purity, and therefore the value, of the desired product(s).

The patent FR2581381 describes a method for neutralization of a titanium-based catalytic system in which the raw effluent that is obtained from the dimerization step is brought into contact with an amine that comprises between 5 and 22 carbon atoms. In particular, the amine can be used in a range of a specific molar ratio between the amine and the titanium compound.

Despite the robustness of the methods implementing a step for neutralization with an amine, the use of amine has limits, in particular on the industrial level because of the toxicity thereof.

The patent EP 0221206 describes a method for dimerization of ethylene into but-1-ene, and having a yield and a selectivity that are improved without the formation of secondary product, by implementing a catalytic system that is based on titanium and alkylaluminum optionally in the presence of additive in particular ratios by mass. It is indicated that the dimerization reaction can be halted by the addition of an alcohol that contains 1 to 4 carbon atoms in the reaction mixture.

One skilled in the art is constantly searching for new methods making it possible to improve the dimerization of ethylene into but-1-ene while preserving the selectivity in favor of but-1-ene during post-reaction treatment steps.

Through his research, the applicant developed a new method for treatment of a raw effluent that is obtained directly from a step for dimerization of ethylene into but-1-ene, comprising a step for neutralization of the catalytic system of the raw effluent by using an alcohol of general formula $R^1OH$, in which $R^1$ is selected from among an alkyl group that contains from 6 to 20 carbon atoms, an aryl or aralkyl group that contains from 5 to 30 carbon atoms.

One advantage of the method according to the invention is to improve the yield of but-1-ene of the reaction for dimerization of ethylene by reducing in a significant manner the secondary reactions such as the isomerization of but-1-ene into but-2-ene, or else uncontrolled addition reactions that can occur during contact between the reaction effluent and the catalyst in the flash tanks or the re-boilers of distillation columns that are necessary to the separation of but-1-ene.

Another advantage of the method according to the invention is to provide a method that is robust and economically viable on the industrial level while eliminating environmental problems (toxicity of the neutralization agent, pyrophoric nature of the catalyst residue . . . ) that are linked to the use of an amine-type neutralization agent.

Another advantage of the method according to the invention is to prevent any contamination of the product of interest during the subsequent purification, for example by distillation, by the neutralization agent that is used during the neutralization step.

DEFINITIONS & ABBREVIATIONS

The terms or abbreviations below have the following meanings throughout the description.

Alkyl group is defined as a hydrocarbon chain that comprises between 1 and 20 carbon atoms, denoted $C_1$-$C_{20}$ alkyl, saturated or not, linear or branched, non-cyclic, cyclic or polycyclic, substituted or not.

Aryl group is defined as a group that is aromatic, monocyclic or polycyclic, fused or not, substituted or not, that comprises between 5 and 30 carbon atoms.

Aralkyl is defined as an alkyl that is substituted by an aryl group.

Heteroatom is defined as an atom that is different from carbon, hydrogen, and is non-metallic. A heteroatom can be selected from among oxygen, sulfur, nitrogen, phosphorus, silicon, and halides such as fluorine, chlorine, bromine or iodine.

Raw effluent is defined as the effluent that is obtained directly from the step for dimerization of ethylene into but-1-ene.

Lewis base (denoted BL) is defined as any molecular entity or any corresponding chemical radical that is capable of providing a pair of electrons and therefore able to coordinate with a Lewis acid, thus producing a Lewis acid/base adduct.

Preformed mixture is defined as the mixture that is obtained by the addition of a Lewis-base-type additive and an aluminum compound of general formula $Al(R^3)_m Y_{3-m}$, prior to any use.

The molar ratio between the aluminum compound and the titanium compound will be, unless otherwise indicated, expressed in terms of mol of aluminum per mol of titanium. The molar ratio between the alcohol $R^1OH$ and the aluminum compound will be expressed in terms of mol of oxygen per mol of aluminum.

Alkoxy is defined as a monovalent radical that consists of an alkyl group linked to an oxygen atom, such as the groups $CH_3O-$, $C_2H_5O-$, $C_3H_7O-$.

DETAILED DESCRIPTION OF THE INVENTION

It is specified that—in this entire description—the expressions "that comprise(s) between . . . and . . . ," "that contain(s) from . . . to . . ." should be understood as including the above-cited boundaries.

In terms of this invention, the various embodiments that are presented can be used by themselves or in combination with one another, with no limit on possible combinations.

The invention therefore relates to a method for treatment of the raw effluent that is obtained directly from a step for dimerization of ethylene into but-1-ene that comprises bringing into contact a catalytic composition that comprises at least one titanium compound and at least one preformed mixture between a Lewis-base (BL)-type additive and an aluminum (Al) compound and an ethylene feedstock, in which the treatment of the effluent comprises a step for neutralization of said raw effluent by adding at least one alcohol of general formula $R^1OH$, in pure form or in solution in a solvent, in which $R^1$ is an alkyl that contains from 6 to 20 carbon atoms, an aryl or aralkyl group that contains from 5 to 30 carbon atoms.

Treatment of the Effluent that is Obtained from the Dimerization Step

In accordance with the invention, the raw effluent that is obtained directly from a step for dimerization of ethylene into but-1-ene is treated in a step for neutralization of said effluent by bringing it into contact with at least one alcohol of general formula $R^1OH$, in which $R^1$ is an alkyl group that contains from 6 to 20 carbon atoms (denoted C).

In a preferred embodiment, the group $R^1$ is an alkyl group that contains from 6 to 15 C, preferably from 7 to 14 C, and preferably from 8 to 12 C.

In a preferred embodiment, the group $R^1$ is a branched alkyl.

In another preferred embodiment, the group $R^1$ is a linear alkyl.

In another preferred embodiment, the group $R^1$ is an aryl or aralkyl group that contains from 5 to 30 carbon atoms (denoted C), preferably from 6 to 20 C, preferably 7 to 18 C, and in a preferred manner from 7 to 15.

Preferably, alcohol is selected from among ethyl-2-hexanol, 1-hexanol, 2-hexanol, 3-hexanol, 2-methyl-1-hexanol, 2-ethyl-1-hexanol, 1-heptanol, 2-heptanol, 2-methyl-3-heptanol, 1-octanol, 2-octanol, 3-octanol, 1-decanol, 2-decanol, 3-decanol, 2-ethyl-1-decanol, 1-dodecanol, phenol, 2-methylphenol, 2,6-dimethylphenol, 2,4,6-trimethylphenol, 4-methylphenol, 2-phenylphenol, 2,6-diphenylphenol, 2,4,6-triphenylphenol, 4-phenylphenol, 2-tert-butyl-6-phenylphenol, 2,4-di-tert-butyl-6-phenylphenol, 2,6-diisopropylphenol, 2,6-di-tert-butylphenol, 4-methyl-2,6-di-tert-butylphenol. In a preferred manner, 2-ethyl-1-hexanol will be used.

The alcohol of formula $R^1OH$ according to the invention can be used in pure form or in solution in a solvent or a mixture of solvents that are selected independently from among aliphatic or cycloaliphatic hydrocarbons, such as hexane, cyclohexane, heptane, butane or isobutane, unsaturated hydrocarbons, such as the monoolefins that comprise between 4 and 20 carbon atoms, aromatic hydrocarbons, such as benzene, toluene, orthoxylene, mesitylene, ethylbenzene, chlorinated hydrocarbons, such as chlorobenzene, dichloromethane, or dichloroethane, the solvents of ether type, such as dimethyl ether, dibutyl ether, tetrahydrofuran, 1,4-dioxane.

Advantageously, the solvent(s) is/are selected independently from among cyclohexane, hexane, n-heptane, tetrahydrofuran, and 1,4-dioxane.

The alcohol of formula $R^1OH$ is preferably added to the raw effluent at a temperature of between 20 and 180° C., preferably between 30 and 100° C., in even more preferred manner between 40 and 80° C.

In one embodiment, the addition of the alcohol of formula $R^1OH$ is carried out at a temperature in an interval of plus or minus (+/−) 20° C. relative to the temperature that is used during the dimerization step, preferably +/−15° C., preferably +/−10° C., in a preferred manner +/−5° C., and in a very preferred manner equal to the temperature of the dimerization step.

In another embodiment, the addition of the alcohol of formula $R^1OH$ is carried out at a temperature that is equal to the temperature that is used during the dimerization step.

The alcohol of formula $R^1OH$ is preferably added to the raw effluent at a pressure of between 0.5 and 15.0 MPa, preferably between 1.0 and 10.0 MPa, and in an even more preferred manner between 1.5 and 5.0 MPa.

In one embodiment, the addition of alcohol of formula $R^1OH$ is carried out at a pressure in an interval of plus or minus (+/−) 2.0 MPa relative to the pressure that is used during the dimerization step, preferably in an interval of plus or minus (+/−) 1.0 MPa, preferably in an interval of plus or minus (+/−) 0.5 MPa, and in a preferred manner equal to the pressure of the dimerization step.

The bringing into contact of the alcohol of formula $R^1OH$ and the raw effluent is implemented by any means known to one skilled in the art that makes it possible to mix two liquids in an area in which the stirring and the dwell time are adequate to allow the neutralization step to be carried out.

Preferably, the alcohol of formula $R^1OH$ is added to the raw effluent that is obtained from the dimerization step in a molar ratio with the aluminum compound that is contained in said effluent ($R^1OH/Al$) that is greater than or equal to 0.1, preferably greater than or equal to 0.5, preferably greater than or equal to 1.0, preferably greater than or equal to 2.0, preferably greater than or equal to 3.0. In a preferred manner, the molar ratio ($R^1OH/Al$) is between 0.1 and 10.0, preferably between 0.5 and 8.0, preferably between 1.0 and 5.0, and in a very preferred manner between 1.0 and 3.0.

In a particular variant of the invention, the effluent that is neutralized by the method according to the invention is subjected to at least a subsequent step for separation of the deactivated catalyst, by any known method and preferably by evaporation, and a subsequent step for separation of the products in the reaction effluent in a separation section.

Step for Dimerization of Ethylene

The raw effluent that is treated in accordance with the invention is obtained at the end of a step for dimerization of ethylene that comprises bringing into contact a catalytic composition that comprises at least one titanium compound of general formula $[Ti(OR^2)_4]$ and at least one preformed mixture between a Lewis-base (BL)-type additive and an aluminum (Al) compound of general formula $Al(R^3)_m Y_{3-m}$, and an ethylene feedstock.

The titanium compounds correspond to the general formula [Ti(OR$^2$)$_4$], in which R$^2$ is independently selected from among
- a linear or branched alkyl group, containing from 2 to 20 carbon atoms, preferably between 2 and 15 C, preferably between 2 and 10 C, and in a very preferred manner between 2 and 8 C. The group R$^2$ can optionally be substituted by a heteroatom that is selected from among a nitrogen, a phosphorus, a sulfur, or an oxygen, substituted or not,
- an aryl group that is substituted or not by one or more alkyl, aryl groups comprising from 2 to 30 carbon atoms. The radical R$^2$ can comprise substituents based on heteroatoms that contain nitrogen, phosphorus, sulfur and oxygen.

Preferably, R$^2$ is selected from among ethyl, isopropyl, n-butyl, sec-butyl, tert-butyl, hexyl, 2-ethyl-hexyl, phenoxy, 2-methylphenoxy, 2,6-dimethylphenoxy, 2,4,6-trimethylphenoxy, 4-methylphenoxy, 2-phenolphenoxy, 2,6-diphenylphenoxy, 2,4,6-triphenylphenoxy, 4-phenylphenoxy, 2-tert-butyl-6-phenylphenoxy, 2,4-di-tert-butyl-6-phenylphenoxy, 2,6-diisopropylphenoxy, 2,6-di-tert-butylphenoxy, 4-methyl-2,6-di-tert-butylphenoxy, 2,6-dichloro-4-tert-butylphenoxy and 2,6-dibromo-4-tert-butylphenoxy, the biphenoxy radical, binaphthoxy, 1,8-naphthalene-dioxy.

The preformed "BL/Al" mixture is obtained by bringing into contact a Lewis-base-type additive and an aluminum compound of general formula Al(R$^3$)$_m$Y$_{3-m}$, separately from the other compounds of the catalytic composition, and prior to their use in said catalytic composition.

Preferably, the "BL/Al" molar ratio between a Lewis-base (BL)-type additive and an aluminum (Al) compound is greater than 0.5, preferably greater than 1.0, preferably between 0.5 and 20.0, preferably between 1.0 and 20.0, in a preferred manner between 0.5 and 5.0, in a more preferred manner between 1.0 and 2.0.

The aluminum compounds are represented by the general formula Al(R$^3$)$_m$Y$_{3-m}$, in which
- R$^3$ is an alkyl or an aryl, preferably alkyl that contains from 1 to 6 carbon atoms,
- Y is selected from among a chlorine atom or a bromine atom, an alkoxy group that contains from 1 to 6 carbon atoms, preferably a chlorine atom,
- m is a whole number between 1 and 3.

Preferably, the aluminum compound is selected from the group that is formed by dichloroethylaluminum (EtAlCl$_2$), ethylaluminum sesquichloride (Et$_3$Al$_2$Cl$_3$), chlorodiethylaluminum (Et$_2$AlCl), chlorodiisobutylaluminum (i-Bu$_2$AlCl), triethylaluminum (AlEt$_3$), tripropylaluminum (Al(n-Pr)$_3$), triisobutylaluminum (Al(i-Bu)$_3$), diethylethoxy aluminum (Et$_2$AlOEt), dimethylethoxy aluminum (Me$_2$AlOEt). The preferred aluminum compound is triethylaluminum (AlEt$_3$).

The Lewis-base-type additive of the catalytic composition that is used in the method according to the invention is advantageously selected independently from among the compounds of the following types: ether, amine, phosphine, sulfide, cyclic or non-cyclic, substituted or not by the following groups: alkyl, aryl, aralkyl comprising from 2 to 30 carbon atoms.

The ether-type compounds are advantageously selected from among the monoethers and the polyethers. Preferably, the preferred ether-type compounds are selected from among diethyl ether, diisopropyl ether, dibutyl ether, diphenyl ether, 2-methoxy-2-methylpropane, 2-methoxy-2-methylbutane, 2,2-dimethoxypropane, 2,2-di(ethyl-2-hexyloxy) propane, 2,5-dihydrofuran, tetrahydrofuran, 2-methoxytetrahydrofuran, 2-methyltetrahydrofuran, 3-methyltetrahydrofuran, 2,3-dihydropyran, tetrahydropyran, 1,3-dioxolane, 1,3-dioxane, 1,4-ioxane, dimethoxyethane, di(2-methoxyethyl)ether, and benzofuran, glyme, diglyme, taken by themselves or in a mixture.

The amine-type compounds are advantageously selected from among monoamines, di-, tri-, and polyamines, imines, diimines, pyridines, bipyridines, imidazoles, pyrroles, pyrazoles. Preferably, the preferred amine-type compounds are selected from among trimethylamine, triethylamine, pyridine, 2-methylpyridine, 3-methylpyridine, 4-methylpyridine, 2-methoxypyridine, 3-methoxypyridine, 4-methoxypyridine, 2-fluoropyridine, 3-fluoropyridine, 3-(trifluoromethyl)pyridine, 2-phenylpyridine, 3-phenylpyridine, 2-benzylpyridine, 3,5-dimethylpyridine, 2,6-di-tert-butylpyridine, and 2,6-diphenylpyridine, quinoline, 1,10-phenanthroline, N-methylpyrrole, N-butylpyrrole, N-methylimidazole, N-butylimidazole, 2,2'-bipyridine, N,N'-dimethyl-ethane-1,2-diimine, N,N'-di-t-butyl-ethane-1,2-diimine, N,N'-di-t-butyl-butane-2,3-diimine, N,N'-diphenyl-ethane-1,2-diimine, N,N'-bis-(dimethyl-2,6-phenyl)-ethane-1,2-diimine, N,N'-bis-(diisopropyl-2,6-phenyl)-ethane-1,2-diimine, N,N'-diphenyl-butane-2,3-diimine, N,N'-bis-(dimethyl-2,6-phenyl)-butane-2,3-diimine, N,N'-bis-(diisopropyl-2,6-phenyl)-butane-2,3-diimine.

The phosphine-type compounds are advantageously selected from among phosphines, polyphosphines, phosphine oxides, phosphites, phosphonites and phosphinites. Preferably, the phosphine-type compounds are selected from among tributylphosphine, triisopropylphosphine, tricyclohexylphosphine, triphenylphosphine, tris(o-tolyl)phosphine, bis(diphenylphosphino)ethane, trioctylphosphine oxide, triphenylphosphine oxide, triphenyl phosphite.

The sulfide-type compounds are advantageously selected from among monosulfides and polysulfides. Preferably, the preferred sulfide-type compounds are selected from among diethyl sulfide, dimethyl disulfide, tetrahydrothiophene, 2-methylthiophene, 3-methylthiophene, 2-methoxythiophene, 3-methoxythiophene.

According to a preferred preparation method, the mixture that is preformed between the Lewis-base-type additive and the aluminum compound is produced by adding an amount of Lewis-base-type additive to the aluminum compound. Preferably, this addition is carried out in a dilute medium by using a solvent. In this case, the solvent that is used is advantageously selected from the group that is formed by the aliphatic and cycloaliphatic hydrocarbons, such as hexane, cyclohexane, and heptane. This mixture is advantageously produced at a temperature of between −80° C., and +200° C., preferably between −40° C. and +100° C., for example at a temperature that is close to ambient temperature (between 15 and 30° C.).

Preferably, the preformed "BL/Al" mixture is obtained by adding a stoichiometric amount of the Lewis-base-type additive to the aluminum compound so as to form an adduct called preformed mixture. Advantageously, said addition is carried out in a dilute medium by using a solvent that is selected from among the group that is formed by aliphatic and cycloaliphatic hydrocarbons, such as hexane, cyclohexane, heptane, and at a temperature of between −80° C. and +200° C., preferably between −40° C. and +100° C.

The titanium compound can be used in a mixture with a hydrocarbon-type solvent that is selected from the group that is formed by aliphatic and cycloaliphatic hydrocarbons, such as hexane, cyclohexane, heptane, butane or isobutane; by an unsaturated hydrocarbon, such as a monoolefin or a diolefin that comprises, for example, from 4 to 20 carbon atoms; by an aromatic hydrocarbon, such as benzene, toluene, orthoxylene, mesitylene, ethylbenzene; by a chlorinated hydrocarbon such as chlorobenzene or dichloromethane, or with an ether-type solvent, such as dimethyl ether, dibutyl ether, tetrahydrofuran, 1,4-dioxane, in pure form or in a mixture. The aliphatic hydrocarbons, such as cyclohexane or n-heptane, and the ethers, such as tetrahydrofuran and 1,4-dioxane, are advantageously used. The mixing can be carried out under an atmosphere of ethylene or inert gas.

In the case where the titanium compound is used mixed with a hydrocarbon-type solvent, said mixture is advantageously used in a volumetric ratio between the solvent and the titanium compound of between 100/1 and 1/1 (vol/vol).

In the case where the titanium compound is used mixed with an ether-type additive, said mixture is advantageously used in a molar ratio between the solvent and the titanium compound of between 20/1 and 1/1 (mol/mol), preferably between 15/1 and 1/1, preferably between 10/1 and 1/1, preferably between 8/1 and 1/1, in a preferred manner between 3/1 and 1/1, and in a very preferred manner is equal to 4/1.

The step for dimerization of ethylene is advantageously implemented at a total pressure of between 0.5 and 20.0 MPa, preferably between 0.5 and 15.0 MPa, preferably between 1.0 and 10.0 MPa, and at a temperature of between 20 and 180° C., preferably between 30 and 140° C., preferably between 40 and 100° C., in an even more preferred manner between 45 and 80° C.

The molar ratio between, on the one hand, the preformed mixture that comprises the aluminum compound and the Lewis-base-type additive, and, on the other hand, the titanium compound of the catalytic composition is implemented such that the molar ratio between the aluminum compound and the titanium compound is between 1/1 and 100/1 (mol/mol), preferably between 1/1 and 50/1, preferably between 1/1 and 10/1, preferably between 1/1 and 5/1, and in a preferred manner between 2/1 and 4/1.

The concentration of titanium in the catalytic solution is advantageously between $1.10^{-9}$ and 1.0 mol/L, preferably between $1.10^{-6}$ and 0.5 mol/L.

According to an embodiment, the step for dimerization of ethylene is implemented intermittently. Selected amounts of solutions of the titanium compound and of the preformed mixture between the Lewis-base-type additive and the aluminum compound are introduced into a reactor that is equipped with the usual devices for stirring, heating, and cooling, and then pressurization is advantageously done by ethylene at the desired pressure, and the temperature is advantageously adjusted to the desired value. The dimerization reactor is kept at constant pressure by the introduction of ethylene until the total volume of liquid that is produced represents, for example, from 2 to 50 times the volume of the solution that comprises the catalytic composition that was originally introduced. The catalyst is then neutralized according to the method of the invention, and then the products of the reaction and the solvent are drawn off and separated.

According to another embodiment, the reaction for oligomerization and in particular for dimerization of ethylene is implemented continuously.

In a first variant, the following are injected separately into a reactor that is kept under constant pressure of ethylene: on the one hand, the titanium compound, and, on the other hand, the mixture that is preformed between the Lewis-base-type additive and the aluminum compound. Said reactor is stirred by the conventional mechanical means known to one skilled in the art or by an external recirculation. The temperature and the pressure of ethylene are kept constant at desired values by using conventional means known to one skilled in the art. The reaction mixture is drawn off by means of a valve that is controlled at the liquid level in such a way as to keep the latter constant. The catalyst is neutralized continuously according to the method of the invention, and then the products that are obtained from the reaction as well as the solvent are separated, for example by distillation. The ethylene that has not been transformed can be recycled in the reactor. The catalyst residue included in a heavy fraction can be incinerated.

In a second variant, the following are injected into a first reactor/mixer: on the one hand, the titanium compound, and, on the other hand, the mixture that is preformed between the Lewis-base-type additive and the aluminum compound; said mixture is then introduced continuously into a reactor that is kept under constant pressure of ethylene. Said mixture that is produced in the first reactor/mixer can be produced under an inert atmosphere or under an ethylene atmosphere. The reaction mixture is drawn off by means of a valve controlled at the liquid level so as to keep the latter constant. The catalyst is neutralized continuously according to the invention, and then the products that are obtained from the reaction as well as the solvent are separated, for example by distillation. The ethylene that has not been transformed can be recycled in the reactor. The catalyst residue included in a heavy fraction can be incinerated.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding application No. FR 1761630, filed Dec. 5, 2017 are incorporated by reference herein.

EXAMPLES

The following examples illustrate the invention without limiting the scope thereof.

Example 1

Test for Dimerization of Ethylene into But-1-ene Followed by a Rise in Temperature without Preliminary Neutralization of the Raw Effluent by an Alcohol (Non-compliant)

The reaction is carried out in a stainless steel autoclave with a useful volume of 100 mL, equipped with electrical heating and a system for cooling by external circulation of compressed air so as to regulate the reaction temperature. Stirring is ensured by a Rushton blade with a magnetic drive. The following are introduced into this reactor under an ethylene atmosphere and at ambient temperature: 15.0 mL of n-heptane as well as 0.3 mmol of the mixture "Ti(O"Bu)$_4$/4THF" that was previously diluted in n-heptane (5.0 mL of a solution with 0.06 mol/L of Ti). Once the temperature of the reactor is brought to 53° C., 0.9 mmol of co-catalyst "AlEt$_3$.THF" (1/1 mol) that was previously diluted in n-heptane (5.0 mL of the solution with 0.18 mol/L of Al) is introduced under an ethylene atmosphere. The pressure of ethylene is kept at 23.0 MPa and the temperature at 53° C. After 19 minutes of reaction, consumption of ethylene that is observed is 15.1 g. At this stage, the introduction of ethylene is halted, and the reactor is cooled to 25° C. The analysis of the effluent of the reactor by gas phase chromatography gives us the following composition: 96% butenes (including 99.3% butene-1), 3% hexenes, and approximately 1% higher olefins.

The temperature of the reactor is then brought to 150° C. for one hour in such a way as to simulate the operating conditions undergone by the reaction mixture in the section for distillation and for separation of but-1-ene. The reactor is then cooled to 25° C. The analysis of the effluent from the reactor by gas phrase chromatography provides us with the following composition: 82% butenes (including only 42% but-1-ene), 12% hexenes, and 6% higher olefins.

Example 2

Test for Dimerization of Ethylene into But-1-ene Followed by a Rise in Temperature after Neutralization of the Crude Effluent by 2-Ethylhexanol (in Accordance with the Invention)

The reaction is carried out in a stainless steel autoclave with a useful volume of 100 mL, equipped with electrical heating and a system for cooling by circulation of compressed air so as to regulate the reaction temperature. Stirring is ensured by a Rushton blade with a magnetic drive. The following are introduced into this reactor under an ethylene atmosphere and at ambient temperature: 15.0 mL of n-heptane as well as 0.3 mmol of the mixture "Ti(OnBu)$_4$/ 4THF" that was previously diluted in n-heptane (5.0 mL of a solution with 0.06 mol/L of Ti). Once the temperature of the reactor is brought to 53° C., 0.9 mmol of co-catalyst "AlEt$_3$.THF" (1/1 mol) that was previously diluted in n-heptane (5.0 mL of a solution with 0.18 mol/L of Al) is introduced under an ethylene atmosphere. The pressure of ethylene is kept at 23.0 MPa and the temperature at 53° C. After 23 minutes of reaction, consumption of ethylene that is observed is 15.7 g, reflecting the presence in this step of a mixture with a composition that is similar to that of Example 1. At this stage, 0.9 mmol (1.0 eq./Al) of 2-ethyl hexanol that was previously diluted in n-heptane is injected. This injection is carried out by means of an SAS under ethylene pressure. Following this operation, the introduction of ethylene is halted, and the temperature of the reactor is brought to 150° C. for 1 hour in such a way as to simulate the operating conditions undergone by the reaction mixture in the section for distillation and separation of but-1-ene. The reactor is then cooled to 25° C. The analysis of the effluent of the reactor by gas phase chromatography gives us the following composition: 95% butenes (including 99.3% but-1-ene), 4% hexenes, and <1% higher olefins.

Example 3

Test for Dimerization of Ethylene into But-1-ene Followed by a Rise in Temperature after Neutralization of the Raw Effluent by 2-Ethylhexanol (in Accordance with the Invention)

The reaction is carried out as in Example 3 except that 3.0 eq. of 2-ethylhexanol is injected during the step for neutralization of the catalytic system. The composition of the products that are obtained is as follows: 95% butenes (including 99.4% but-1-ene), 4% hexenes, and <1% higher olefins.

Example 4

Test for Dimerization of Ethylene into But-1-ene Followed by a Rise in Temperature after Neutralization of the Raw Effluent by 1-Dodecanol (in Accordance with the Invention)

The reaction is carried out as in Example 3 except that 3.0 eq. of 1-dodecanol is injected during the step for neutralization of the catalytic system. The composition of the products that are obtained is as follows: 94% butenes (including 99.4% but-1-ene), 4% hexenes, and <1% higher olefins.

The examples that are presented here show that the neutralization of the reaction effluent by an alcohol is effective even under the temperature conditions that the reaction mixture experiences in the section for distillation and separation of but-1-ene. In the absence of this neutralization operation, a drastic reduction in but-1-ene selectivity is observed.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. Method for treatment of the raw effluent that is obtained directly from a step for dimerization of ethylene into but-1-ene that comprises bringing into contact a catalytic composition that comprises at least one titanium compound of general formula [Ti(OR$^2$)$_4$] and at least one preformed mixture between a Lewis-base (BL)-type additive and an aluminum (Al) compound of general formula Al(R$^3$)mY$_{3-m}$, and an ethylene feedstock, wherein the treatment of the effluent comprises a step for neutralization of said raw effluent by adding at least one alcohol of general formula R$^1$OH, in pure form or in solution in a solvent, wherein R$^1$ is an alkyl group, linear or branched, which contains from 6 to 20 carbon atoms, or an aryl or aralkyl group that contains from 5 to 30 carbon atoms,
   wherein R$^2$ is a linear or branched alkyl group, containing from 2 to 20 carbon atoms,
   wherein R$^3$ is an alkyl or an aryl,
   wherein m is a whole number between 1 and 3, and
   wherein Y is a chlorine atom a bromine atom, or an alkoxy group that contains from 1 to 6 carbon atoms.

2. Method according to claim 1, wherein R$^1$ is selected from the group consisting of an alkyl group that comprises between 6 and 15carbon atoms, and an aryl or aralkyl group that contains from 6 to 20 C.

3. Method according to claim 1, in which R$^1$ is a branched alkyl group.

4. Method according to claim 1, in which R$^1$OH is selected from the group consisting of ethyl-2-hexanol, 1-hexanol, 2-hexanol, 3-hexanol, 2-methyl-1-hexanol, 2-ethyl-1-hexanol, 1-heptanol, 2-heptanol, 2-methyl-3-heptanol, 1-octanol, 2-octanol, 3-octanol, 1-decanol, 2-decanol, 3-decanol, 2-ethyl-1-decanol, 1-dodecanol, phenol, 2-methylphenol, 2,6-dimethylphenol, 2,4,6-trimethylphenol, 4-methylphenol, 2-phenylphenol, 2,6-diphenylphenol, 2,4,6-triphenylphenol, 4-phenylphenol, 2-tert-butyl-6-phenylphenol, 2,4-di-tert-butyl-6-phenylphenol, 2,6-diisopropylphenol, 2,6-di-tert-butylphenol, 4-methyl-2,6-di-tert-butylphenol.

5. Method according to claim 1, in which the alcohol $R^1OH$ is used in solution in a solvent or a mixture of solvents that are selected independently from among
- aliphatic or cycloaliphatic hydrocarbons,
- unsaturated hydrocarbons,
- aromatic hydrocarbons,
- chlorinated hydrocarbons,
- the solvents of ether type.

6. Method according to claim 1, in which the addition of the alcohol of formula $R^1OH$ is carried out at a temperature that is less than or greater than 20° C. relative to the temperature that is used during the dimerization step.

7. Method according to claim 1, in which the addition of the alcohol of formula $R^1OH$ is carried out at a pressure that is less than or greater than 2.0 MPa relative to the pressure that is used during the dimerization step.

8. Method according to claim 1, in which the alcohol of formula $R^1OH$ is added to the raw effluent at a pressure of between 0.5 and 15.0 MPa.

9. Method according to claim 1, in which the alcohol of formula $R^1OH$ is added to the raw effluent that is obtained from the dimerization step in a molar ratio with the aluminum compound that is contained in the effluent ($R^1OHAl$) that is greater than or equal to 0.1.

10. Method according to claim 1, in which the titanium compound corresponds to the general formula $[Ti(OR^2)_4]$, in which $R^2$ is independently selected from among
- a linear or branched alkyl group, containing from 2 to 20 carbon atoms, and optionally substituted by a substituted or unsubstituted heteroatom selected from the group consisting of a nitrogen, a phosphorus, a sulfur, and an oxygen; or
- an aryl group comprising from 2 to 30 carbon atoms, by alkyl, or aryl groups wherein said alkyl and aryl groups optionally comprise at least one heteroatom that contains nitrogen, phosphorus, sulfur and oxygen.

11. Method according to claim 1, in which the aluminum compound corresponds to the general formula $Al(R^3)_m Y_{3-m}$, in which $R^3$ is an alkyl or an aryl, Y is a chlorine atom, a bromine atom, or an alkoxy group that contains from 1 to 6 carbon atoms, and m is a whole number between 1 and 3.

12. Method according to claim 1, in which the Lewis-base-type additive is selected from the group consisting of cyclic or non-cyclic ether, cyclic or non-cyclic amine, cyclic or non-cyclic phosphine, and cyclic or non-cyclic sulfide, and wherein the Lewis-base-type additive is unsubstituted or substituted by alkyl, aryl, or aralkyl comprising from 2 to 30 carbon atoms.

13. Method according to claim 1, in which the "BL/Al" molar ratio between a Lewis-base (BL)-type additive and an aluminum compound (Al) is greater than 0.5.

14. Method according to claim 1, wherein the molar ratio of the preformed mixture that comprises the aluminum compound and the Lewis-base-type additive, to, the titanium compound of the catalytic composition is implemented such that the molar ratio between the aluminum compound and the titanium compound is between 1/1 and 100/1 (mol/mol).

15. Method according to claim 1, in which the titanium compound is used in a mixture with an ether-type additive in a molar ratio between the additive and the titanium compound of between 20/1 and 1/1 (mol/mol).

16. Method according to claim 5, wherein the aliphatic or cycloaliphatic hydrocarbons are hexane, cyclohexane, heptane, butane or isobutane, wherein the unsaturated hydrocarbons are monoolefins or diolefins that comprise between 4 and 20 carbon atoms, wherein the aromatic hydrocarbons are benzene, toluene, orthoxylene, mesitylene, or ethylbenzene, wherein the chlorinated hydrocarbons are chlorobenzene or dichloromethane, and wherein the solvents of ether type are dimethyl ether, dibutyl ether, tetrahydrofuran, 1, 4-dioxane.

17. Method according to claim 11, wherein $R^3$ is alkyl that contains from 1 to 6 carbon atoms.

18. Method according to claim 13, wherein the "BL/Al" molar ratio between a Lewis-base (BL)-type additive and an aluminum compound (Al) is between 0.5 and 20.0.

* * * * *